(12) United States Patent
Piryk et al.

(10) Patent No.: US 11,679,238 B1
(45) Date of Patent: Jun. 20, 2023

(54) GUIDEWIRE RETRACTION DEVICE (71) Applicants: Christopher Piryk, St. Petersburg, FL (US); Alexis Bushman, St. Petersburg, FL (US)

(72) Inventors: Christopher Piryk, St. Petersburg, FL (US); Alexis Bushman, St. Petersburg, FL (US)

( * ) Notice: Subject to any disclaimer, the term of this patent is extended or adjusted under 35 U.S.C. 154(b) by 0 days.

(21) Appl. No.: 17/661,387

(22) Filed: Apr. 29, 2022

Related U.S. Application Data (63) Continuation of application No. 17/549,974, filed on Dec. 14, 2021, now Pat. No. 11,369,775.

(51) Int. Cl.
*A61M 25/09* (2006.01)
*A61M 25/06* (2006.01)

(52) U.S. Cl.
CPC .. *A61M 25/09041* (2013.01); *A61M 25/0905* (2013.01); *A61M 25/065* (2013.01); *A61M 2025/09116* (2013.01)

(58) Field of Classification Search
CPC .......... A61M 25/09041; A61M 25/065; A61M 25/0905; A61M 25/09; A61M 2025/09116; A61M 2025/09125
See application file for complete search history.

(56) References Cited

U.S. PATENT DOCUMENTS

| | | | | |
|---|---|---|---|---|
| 4,716,757 A * | 1/1988 | McGregor | ...... | A61M 25/09041 72/383 |
| 5,318,541 A * | 6/1994 | Viera | ...... | A61M 25/09041 604/159 |
| 5,454,785 A * | 10/1995 | Smith | ...... | A61M 29/02 604/510 |
| 5,707,363 A * | 1/1998 | Crawford | ...... | A61M 25/01 604/177 |
| 5,978,699 A * | 11/1999 | Fehse | ...... | A61M 25/09041 600/585 |
| 6,277,100 B1 * | 8/2001 | Raulerson | ...... | A61M 25/0693 604/167.03 |
| 2003/0036712 A1 * | 2/2003 | Heh | ...... | A61M 25/09041 604/95.04 |
| 2004/0082880 A1 * | 4/2004 | Heh | ...... | A61M 25/09041 604/95.04 |
| 2005/0171568 A1 * | 8/2005 | Duffy | ...... | A61M 25/09041 606/191 |

(Continued)

*Primary Examiner* — Nilay J Shah
(74) *Attorney, Agent, or Firm* — Tiffany C. Miller; Inventions International Inc.

(57) ABSTRACT

A guidewire retraction device having a first support structure located opposite a second support structure. The first support structure has a primary bore traversing the length of the first support structure. The first support structure has a first opening bordering a first ramp. The first ramp is connected to the primary bore. A second support structure has a secondary bore traversing the length of the second support structure. The second support structure has a second opening bordering a second ramp. The second ramp is connected to the secondary bore. The first ramp of the first support structure and the second ramp of the second support structure are configured to receive a guidewire. A rotation element is rotated in a first direction to orient the guidewire in a retracted orientation. The rotation element is rotated in a second direction to orient the guidewire in an advanced orientation.

17 Claims, 8 Drawing Sheets

(56) References Cited

U.S. PATENT DOCUMENTS

| | | | | |
|---|---|---|---|---|
| 2006/0025721 A1* | 2/2006 | Duffy | ............ | A61M 25/09041 604/164.12 |
| 2006/0253048 A1* | 11/2006 | Jones | ............ | A61M 25/09041 604/528 |
| 2015/0290433 A1* | 10/2015 | Holbert | ........... | A61M 25/09041 604/528 |

* cited by examiner

GUIDEWIRE RETRACTION DEVICE

CROSS REFERENCE TO RELATED APPLICATIONS

This application is a Continuation Utility Application entitled, "Guidewire Retraction Device", which claims priority to co-pending Original Non-Provisional Utility U.S. patent application Ser. No. 17/549,974 filed Dec. 14, 2021, entitled, "Systems and Methods for Guidewire Retraction".

BACKGROUND OF THE INVENTION

1. Field of the Invention

This innovation relates, generally, to systems and methods for guidewire retraction. More particularly, it relates to a removable retraction device configured to connect to a tubing structure and receive a guidewire during central venous cannulation.

2. Background Art

The Seldinger technique is implemented during many central venous cannulation procedures including, but not limited to, radiographic medical imaging, chest drain and/or central venous catheter installation, percutaneous endoscopic gastrostomy tube insertion, and lead insertion for an implantable medical device including, but not limited to, an artificial pacemaker or a cardioverter-defibrillator. In a first step of the Seldinger technique, a sharp hollow needle is provided. It is known that a user punctures and inserts a sharp hollow needle into a predetermined blood vessel, a cavity, or an organ. A guidewire having a substantially radiused end portion is inserted and advanced through the lumen portion of the hollow needle. A user is required to hold the guidewire continuously to prevent inadvertent movement and/or loss of the guidewire. The hollow needle is then withdrawn and replaced by a tubing structure including, but not limited to, a catheter, a peripherally inserted central catheter line, a feeding tube, a drainage tube, a dilator, a sheath, an introducer sheath, and/or a blunt cannula. In an example, a dilator is inserted through the puncture of a patient and is used to introduce a catheter passed over the guidewire into the desired blood vessel, cavity, or organ. After the aforementioned tubing structure is passed over the guidewire into the predetermined blood vessel, cavity, or organ, the guidewire is then removed. Upon completion of the central venous catheterization procedure, the tubing structure is secured in place. The tubing material establishes venous access for administration of including, but not limited to, a medication and/or resuscitation.

Although percutaneous catheterization of central veins is a standard procedure in today's medical field, the problem of an inadvertent intravascular insertion of the full length of a guidewire has resulted from numerous predisposing factors originating from a break in procedure at one of the most critical steps in the process of central venous catheterization. In particular, this key step requires a user to hold the guidewire continuously to prevent inadvertent movement and/or loss of the guidewire. For example, the user may be an inexperienced operator, the user may not have been paying attention during the critical step of holding the guidewire at all times of the Seldinger technique, the user may not have been sufficiently trained in the Seldinger technique by an authorized supervisor and/or mentor, and/or the user may have been over tired and/or over stressed. Many of these predisposing factors are currently known to contribute to a user releasing the guidewire during the process of central venous catheterization resulting in loss of the guidewire. Thus, it is within the scope of this current invention for a guidewire retainment and retraction device to be incorporated into the method of placement of a central venous catheter to enhance precautionary safety procedures by preventing loss of the guidewire into a patient's body.

It is within the scope of this invention for a user to include, but not be limited to, any person, a surgeon, an anesthesiologist, a certified registered nurse anesthetist, a physician assistant, a physician, a nurse practitioner, a resident medical physician, a health care professional, any individual that has received adequate training to perform such a procedure, or an experienced operator. If a user is safely and correctly performing the Seldinger technique on a patient during central venous cannulation, the guidewire is manually held by the user at all times and at least a portion of the guide wire is extended beyond the surface of a patient's skin to facilitate the handling of the guidewire. In contrast, if a user releases their grasp of the guidewire during the process of performing the Seldinger technique, guidewire loss may occur when the entire guidewire completely advances into a blood vessel, a cavity, or an organ. In particular, the failure of a user to manually retract and remove the guidewire during this procedure is currently known to contribute to guidewire loss. Some primary indicators of guidewire loss includes, but is not limited to, the appearance that a guidewire is missing, resistance to injection via the distal lumen, a decreased backflow from the distal lumen, and/or a visible confirmation of a radiographic image of the guidewire within a patient's body.

As a result of intravascular insertion of a complete guidewire, hereinafter, referred to as guidewire loss, during central venous cannulation, a patient may experience complications including, but not limited to, an embolism, an arrhythmia, vascular damage, thrombosis, or death. Upon determination of a guidewire loss, the full length of the guidewire would need to be retrieved, which may be associated with an invasive surgical procedure, an interventional radiologic procedure, or malpractice and/or other litigation, which may be costly and damaging to the user's reputation. Thus, there is a long felt, yet unfulfilled need for a novel removable guidewire retraction device configured to receive, retain, and retract a guidewire during the central venous cannulation process, thereby, eliminating a step in existing methods of the placement of a central venous catheter. In particular, once the novel removable retraction device is installed over the guidewire, a user is no longer required to manually hold or grasp the guidewire with their hand while performing the novel method of placement of a central venous catheter. A novel removable guidewire retention device prevents guidewire loss and allows a user to use their hand freely during the novel method of placement of a central venous catheter.

Current guidewire advancement devices are configured to advance a guidewire into a needle. The solid housing of existing guidewire advancement devices are not structurally configured for use during guidewire retraction during placement of a central venous catheter. In particular, the proximal end of a guidewire is obstructed when the proximal end of the guidewire is positioned inside of a patient. The distal end of a guidewire may be obstructed from being passed over numerous times during the process of connecting a catheter, for example. A problem exists when guidewire advancement devices in today's market place are not capable of being removed from a guidewire with both ends of the guidewire being obstructed. Thus, there is a need for a guidewire retraction device configured to be removable from at least a portion of exposed guidewire located between the insertion site or puncture of the needle and a distal end of the guidewire while performing a method for placement of a central venous catheter It is known for guidewire loss to occur during central venous cannulation, most frequently after the step in which the guidewire has been advanced through the introductory needle into the patient and the central catheter, for example, is being advanced over the guidewire. In particular, the guidewire is often advanced with a catheter into a patient when the guidewire is not manually grasped and retracted by a user. Further, due to the possibility of a user inadvertently omitting or forgetting to install the novel removable guidewire retraction device to the guidewire, during the Seldinger technique or any other comparable procedure, or any other technique used to perform a central venous cannulation procedure, there is also a need for a tubing structure such as, a catheter having an integrally formed guidewire retraction device connected thereto or a guidewire retraction device configured to removably connect to at least a portion of a tubing structure such as, a catheter.

However, in view of the prior art considered as a whole at the time the present invention was made, it was not obvious to those of ordinary skill in the pertinent art how the identified needs could be fulfilled.

SUMMARY OF THE INVENTION

The long-standing but heretofore unfulfilled need for a guidewire retraction device having a first support structure located opposite a second support structure. The first support structure has a primary bore traversing the length of the first support structure. The first support structure has a first opening bordering a first ramp. The first ramp is connected to the primary bore. A second support structure has a secondary bore traversing the length of the second support structure. The second support structure has a second opening bordering a second ramp. The second ramp is connected to the secondary bore. The first ramp of the first support structure and the second ramp of the second support structure are configured to receive a guidewire. A rotation element is rotated in a first direction to orient the guidewire in a retracted orientation. The rotation element is rotated in a second direction to orient the guidewire in an advanced orientation, and which also includes improvements that overcome the limitations of prior guidewire retraction systems and methods during central venous cannulation is now met by a new, useful, and non-obvious invention.

As used herein, the term "distal" refers to a location of the device closest to a user operating the device and farthest from a patient in connection with whom the device is used when the device is used in its normal operation. The term "proximal" refers to a location of the device that is closest to a patient with whom the device is used when the device is used in normal operation and farthest from a user operating the device.

In a preferred embodiment, a guidewire retraction device has a first support structure located opposite a second support structure. The first structure has a first end located opposite a second end. The first support structure has a primary bore traversing the length of the first support structure. The first support structure has a first opening bordering a first ramp. The first ramp is connected to the primary bore. The primary bore of the first support structure is configured to be removably connected to a proximal portion of a tubing structure. A second support structure has a secondary bore traversing the length of the second support structure. The second support structure has a second opening bordering a second ramp. The second ramp is connected to the secondary bore. The first ramp of the first support structure and the second ramp of the second support structure are configured to receive a guidewire when a guidewire is inserted through the first opening bordering the first ramp and through the second opening bordering the second ramp.

A rotation element is located between the first support structure and the second structure. The rotation element has a shaft. It is within the scope of this invention for the rotation element to include, but not be limited to, a wheel, a sphere, or a disc. The rotation element has a recess configured to retain at least a portion of the guidewire when the guidewire is retained within the primary bore of the first support structure and the secondary bore of the second support structure. The rotation element is configured to be rotated in a first direction toward the first support structure to orient the guidewire in a retracted orientation. It is within the scope of this invention for the guidewire having a retracted orientation to include, but not be limited to, moving the guidewire distally away from a patient, the removal of the guidewire from a patient's body, withdrawing the guidewire in whole or in part from a blood vessel, a cavity, or an organ. The rotation element is configured to be rotated in a second direction toward the second support structure to orient the guidewire in an advanced orientation. It is within the scope of this invention for the guidewire having an advanced orientation to include, but not be limited to, moving the guidewire proximally toward a patient, the insertion of the guidewire into a patient's body, moving the guidewire in whole or in part through and/or into a blood vessel, a cavity, or an organ.

The recess of the rotation element is not in alignment with the primary bore of the first support structure and the secondary bore of the second support structure. The recess of the rotation element is oriented in an elevated position in relation to the primary bore of the first support structure and the secondary bore of the second support structure. The recess traverses the circumference of the rotation element. The elevated position of the recessed track of the rotation element in relation to the primary bore of the first support structure and the secondary bore of the second support structure extends the guidewire out of alignment with the second end of the third portion of the primary bore of the first structure and with the first end of the fourth portion of the secondary bore of the second support structure in such a way that increases the tension of the guidewire, thereby, preventing movement of the guidewire unless a user rotates the rotation element either in a first direction or a second direction. Further, this elevated positioning of the recessed track of the rotation element in relation to the primary bore of the first support structure and the secondary bore of the second support structure orients the guidewire to be retained within the recessed track of the rotation wheel. It is within the scope of this invention for an elevated positioning of the recessed track of the wheel to include, but not be limited to, any position of the rotation element that orients the guidewire to not be aligned with the primary bore of the first support structure and the secondary bore of the second support structure to increase tension of the guidewire. The recessed track of the rotation element has side walls forming a channel or slot traversing the entire circumference of the rotation element. A first shaft support structure is oriented parallel to a second shaft support structure. The shaft of the rotation element is connected to the first support structure and the second support structure. In an example, a first shaft protrudes from a first side of a wheel and a second shaft protrudes from the second side of a wheel.

In an alternate embodiment, the guidewire retraction device can have a handle. The handle is configured for a user to grasp the handle and/or to support at least one finger during use such as, rotation of the rotation element in a first and/or second direction.

In another embodiment, the guidewire retraction device can have a primary bore of the first support structure having a first portion being tapered. The first portion of the primary bore has a first end located opposite a second end. The first end of the first portion of the primary bore has a diameter greater in size than the second end of the first portion of the primary bore to securely receive and retain a tubing structure. The first end of the first portion of the primary bore is located on the first end of the first support structure. The second end of the first portion of the primary bore is connected to a second portion. The second portion of the primary bore has a consistent diameter smaller in size than the second end of the first portion of the primary bore to more tightly retain the guidewire. The second portion of the primary bore is connected to a third portion. The third portion of the primary bore is tapered to allow the guidewire to have a greater range of motion while the guidewire is being captured by the second end of said third portion of the primary bore. The third portion of the primary bore has a first end located opposite a second end. The first end of the third portion of the primary bore has a diameter smaller in size than the second end of the third portion of the primary bore. The second end of the third portion of the primary bore is located on the second end of the first support structure. The second end of the third portion of the primary bore is a first capturing structure configured to catch the guidewire as the guidewire passes over the rotation element when the rotation element is rotated in a first direction so that the guidewire is in a retracted orientation.

The secondary bore of the second support structure has a fourth portion having a first end located opposite a second end. The second end of the fourth portion of the secondary bore is connected to a fifth portion. The fifth portion of the secondary bore is tapered. The fifth portion of the secondary bore has a first end located opposite a second end. The first end of the fifth portion of said secondary bore is connected to the second end of the fourth portion of the secondary bore. The first end of the fifth portion of the secondary bore has a diameter smaller in size than a diameter of the second end of the fifth portion of the secondary bore. The second end of the fifth portion of the secondary bore is located on the said second end of the second support structure. The second end of the fifth portion of the secondary bore has a larger diameter and is a second capturing structure configured to catch the guidewire as the guidewire is inserted into the guidewire retention device.

In a preferred embodiment, both the first capturing structure and second structure have tapered wall surfaces configured for the larger portion of the tapered wall surface to facilitate a guidewire being caught and fed into the guidewire retraction device during installation of the guidewire retraction device onto a guidewire.

In another embodiment, the guidewire retraction device has a rotation element having a plurality of projections located thereon. Further, a plurality of recesses including, but not limited to, pits, and/or hatched score lines may be added to the surface of the rotation element to increase the coefficient of friction as a user rotates the rotation element in a first direction and/or a second direction. It is within the scope of this invention for at least one protrusion or at least one recess be located on any surface of the rotation element including, but not limited to, the recessed track, the slot, the channel, the track, and/or the portion of the wheel configured to be contacted by a user during use.

In yet another embodiment, the second end of the first support structure has a bevel. The first end of the second support structure has a bevel. It is an important aspect of this current invention for a user to be able to visually follow the end of the guidewire while feeding it through the guidewire retraction device during use. As a result of the enhanced visual area created by the bevels of the guidewire retraction device, a user can more accurately determine the length of guidewire that has been retracted and/or advanced through the guidewire retraction device, thus enhancing the efficiency and safety of the procedure.

In an alternate embodiment, a guidewire retraction system for use during central venous cannulation has a guidewire retraction device and a retention cap. The guidewire retraction device described in the first embodiment is included in the guidewire retraction system with the addition of a retention cap. A retention cap is configured to be connected to a distal portion of a tubing structure such as, a catheter. For example, a catheter has one end connected to a guidewire retention device and another end connected to a retention cap during a central venous cannulation procedure to prevent guidewire loss during use. It is within the scope of the current invention for the guidewire device to have a primary bore of a first support structure being configured to removably connect to a proximal end of a tubing structure. The retention cap has an integrally formed capturing structure. The capturing structure has a sidewall and a compartment. At least a portion of the inner wall surface of the sidewall of the capturing structure is configured to have a tapered shape to catch and/or guide the guidewire into the compartment. The retention cap has a substantially central bore located within the compartment of the capturing structure. The substantially central bore traverses through the retention cap. In a first embodiment, the substantially central bore of the retention cap can have a diameter large enough in size for the guidewire to be received by the substantially central bore and having a diameter small enough in size for the guidewire to traverse the length of the substantially central bore of the retention cap by the force of a user applied to the guidewire. In an alternate embodiment, at least a portion of the retention cap can be made of a pliable material such as, rubber. The pliable material is configured to conform to the outer surface of the guidewire to create a seal in which the guidewire may be retained in position until the force of a user rotating the rotation element either advances or retracts the guidewire.

It is an important aspect of this invention to provide a method of performing a central venous cannulation procedure having the steps of first providing a sharp hollow needle. Second, puncturing and inserting the sharp hollow needle into a predetermined blood vessel, a cavity, and/or an organ is required. In a third step, a guidewire is provided having a substantially radiused end portion. In the next step, a user inserts the substantially radiused end portion of the guidewire into the sharp hollow needle. The guidewire is then advanced through the sharp hollow needle. The next step includes a user withdrawing the sharp hollow needle from the blood vessel, a cavity, and/or an organ.

In the next step, a guidewire retraction device of the first embodiment is provided having a first support structure located opposite a second support structure. The first structure has a first end located opposite a second end. The first support structure has a primary bore. The primary bore of the first support structure traverses the length of the first support structure from the first end of the first support structure to the second end of the first support structure. The first support structure has a first opening bordering a first ramp. The first ramp is connected to the primary bore. The primary bore of the first support structure has a first portion being tapered. The first portion of the primary bore has a first end located opposite a second end. The first end of the first portion of the primary bore has a diameter greater in size than the second end of the first portion of the primary bore. The first end of the first portion of the primary bore is located on the first end of the first support structure. The second end of the first portion of the primary bore is connected to a second portion. The second portion of the primary bore has a diameter smaller in size than the second end of the first portion of the primary bore. The second portion of the primary bore is connected to a third portion.

The third portion of the primary bore is tapered. The third portion of the primary bore has a first end located opposite a second end. The first end of the third portion of the primary bore has a diameter smaller in size than the second end of the third portion of the primary bore. The second end of the third portion of the primary bore is located on the second end of the first support structure. The second support structure has a secondary bore. The secondary bore of the second support structure has a fourth portion having a first end located opposite a second end. The second end of the fourth portion of the secondary bore is connected to a fifth portion. The fifth portion of the secondary bore is tapered. The fifth portion of the secondary bore has a first end located opposite a second end. The first end of the fifth portion of the secondary bore is connected to the second end of the fourth portion of the secondary bore. The first end of the fifth portion of the secondary bore has a diameter smaller in size than a diameter of the second end of the fifth portion of the secondary bore. The second end of the fifth portion of the secondary bore is located on the second end of the second support structure. The secondary bore of the second support structure traverses the length of the second support structure from the first end of the second support structure to the second end of the second support structure.

The second support structure has a second opening bordering a second ramp. The second ramp is connected to the secondary bore. The first ramp of the first support structure and the second ramp of the second support structure are configured to receive a guidewire. The guidewire retraction device has a rotation element. A rotation element is located between the first support structure and the second structure. The rotation element has a shaft. It is within the scope of this invention for the rotation element to include, but not be limited to, a wheel, a sphere, or a disc. The rotation element has a recess configured to retain at least a portion of the guidewire when the guidewire is retained within the primary bore of the first support structure and the secondary bore of the second support structure. The rotation element is configured to be rotated in a first direction toward the first support structure to orient the guidewire in a retracted orientation. It is within the scope of this invention for the guidewire having a retracted orientation to include, but not be limited to, moving the guidewire distally away from a patient, the removal of the guidewire from a patient's body, withdrawing the guidewire in whole or in part from a blood vessel, a cavity, or an organ. The rotation element is configured to be rotated in a second direction toward the second support structure to orient the guidewire in an advanced orientation. It is within the scope of this invention for the guidewire having an advanced orientation to include, but not be limited to, moving the guidewire proximally toward a patient, the insertion of the guidewire into a patient's body, moving the guidewire in whole or in part through and/or into a blood vessel, a cavity, or an organ.

In a next step of this novel method, a tubing structure, such as a catheter, is provided having a proximal end and a distal end. Next, the proximal end of the tubing structure is connected to the first end of the first portion of the primary bore of the first support structure of the guidewire retraction device. For example, the catheter tubing is inserted into the primary bore of the guidewire retraction device. In the next step, a retention cap is provided. The retention cap has an integrally formed capture structure. The capture structure has a sidewall forming a cylindrical structure having a compartment. The sidewall is configured to catch and/or guide the guidewire into the compartment. The retention cap has a substantially central bore located within the compartment of the capturing structure. The substantially central bore traverses the retention cap. The substantially central bore of the retention cap has a diameter large enough in size for the guidewire to be received by the substantially central bore and having a diameter small enough in size for the guidewire to traverse the length of the retention cap by the force of a user.

In the next step of the method, a user connects the retention cap to the distal portion of a tubing structure. Next, a user inserts the guidewire through the secondary bore of the second support structure of the guidewire retention device. A user then positions the guidewire within the recess of the rotation element of the guidewire retention device. A user applies the force of at least one finger to the guidewire overlaying the rotation element and rotates the rotation element in a first direction to extend the guidewire through the primary bore of the first support structure until at least a portion of the guidewire protrudes from the retention cap of the distal end of a tubing structure. A user then removes and/or disconnects the guidewire retraction device from the proximal end of the tubing structure. The guidewire is removed from the recess of the rotation element. A user then simultaneously positions the guidewire retained within the primary bore of the first support structure and the secondary bore of the second support structure of the guidewire retraction device through the first ramp of the first support structure and the second ramp of the second support structure, thereby, completely removing the guidewire retraction device from the guidewire.

BRIEF DESCRIPTION OF THE DRAWINGS

For a fuller understanding of the nature and objects of the invention, reference should be made to the following detailed description, taken in connection with the accompanying drawings, in which.

DETAILED DESCRIPTION OF THE PREFERRED EMBODIMENT

In the following detailed description of the preferred embodiments, reference is made to the accompanying drawings, which form a part hereof, and within which are shown by way of illustration specific embodiments by which the invention may be practiced. It is to be understood that other embodiments may be utilized and structural changes may be made without departing from the scope of the invention. Further, the retention cap and/or other components not be drawn to scale. In particular, the threads of the retention cap are configured to secure to the threads (not shown) of an end of a lumen of a catheter.

Figure 1:
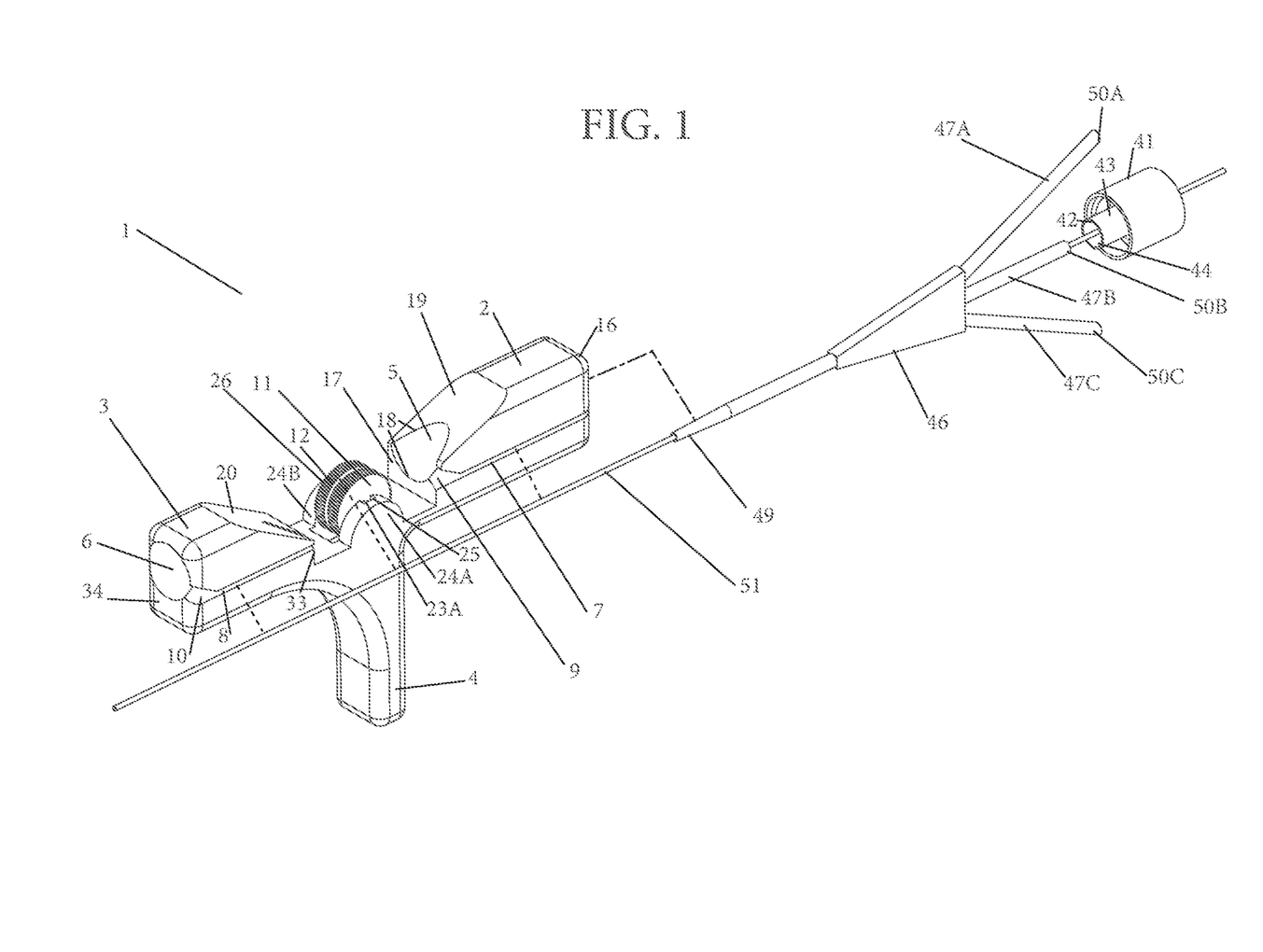
FIG. 1 is an exploded view of the proximal end of the novel guidewire retraction device, the guidewire, a triple lumen catheter, and a retention cap.
Figure 2:
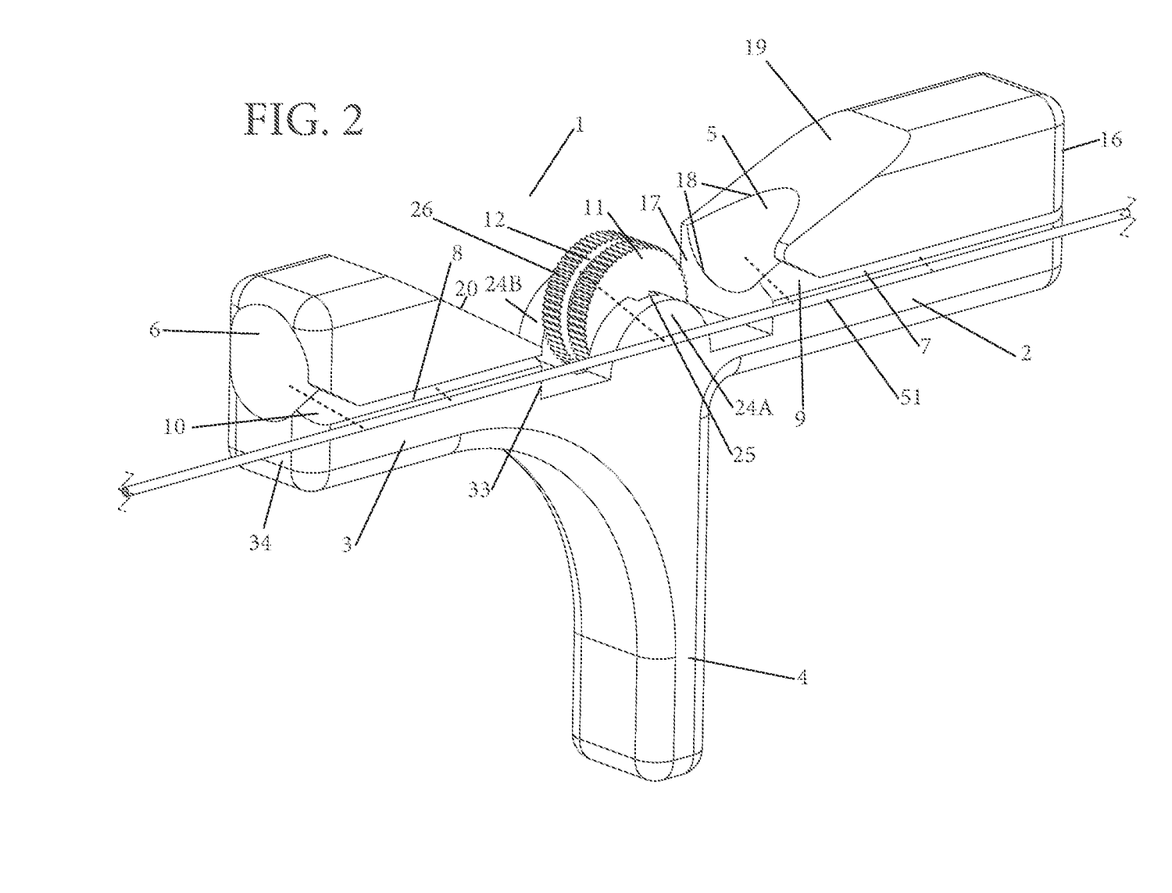
FIG. 2 is a perspective view of the proximal end of the novel guidewire retraction device configured to receive a guidewire.

FIGS. 1 and 2 illustrate guidewire retraction device 1, having first support structure 2 located opposite second support structure 3. Guidewire retraction device 1 has handle 4 (FIGS. 1-7). First support structure 2 has first end 16 located opposite second end 17. First support structure 2 has primary bore 5. Second support structure 3 has secondary bore 6. Secondary bore 6 of second support structure 3 traverses the length of second support structure 3 from first end 33 (FIGS. 1-5) of second support structure 3 to second end 34 (FIGS. 1-5) of second support structure 3.

Figure 3:
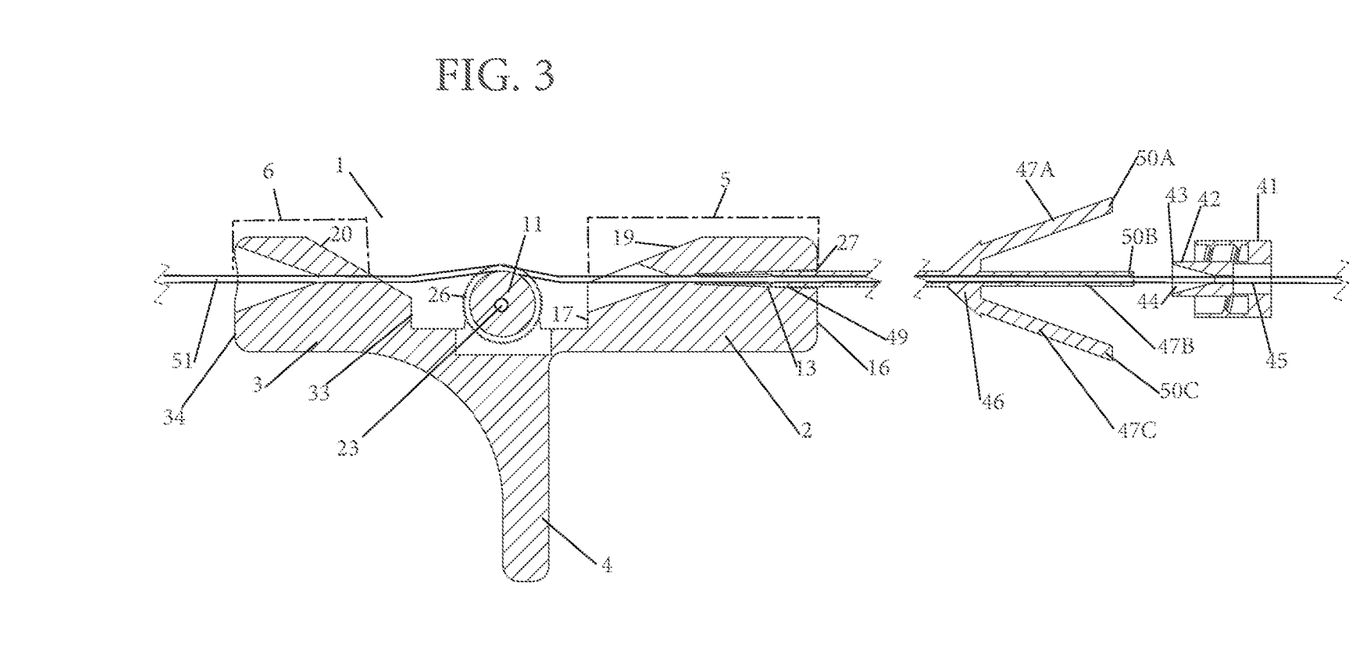
FIG. 3 is a side cut-away view of the novel guidewire retraction device retaining a guidewire, having the proximal end of a triple lumen catheter connected to the distal portion of the guidewire retraction device, and having a novel retention cap connected to a lumen of the catheter.
Figure 4:
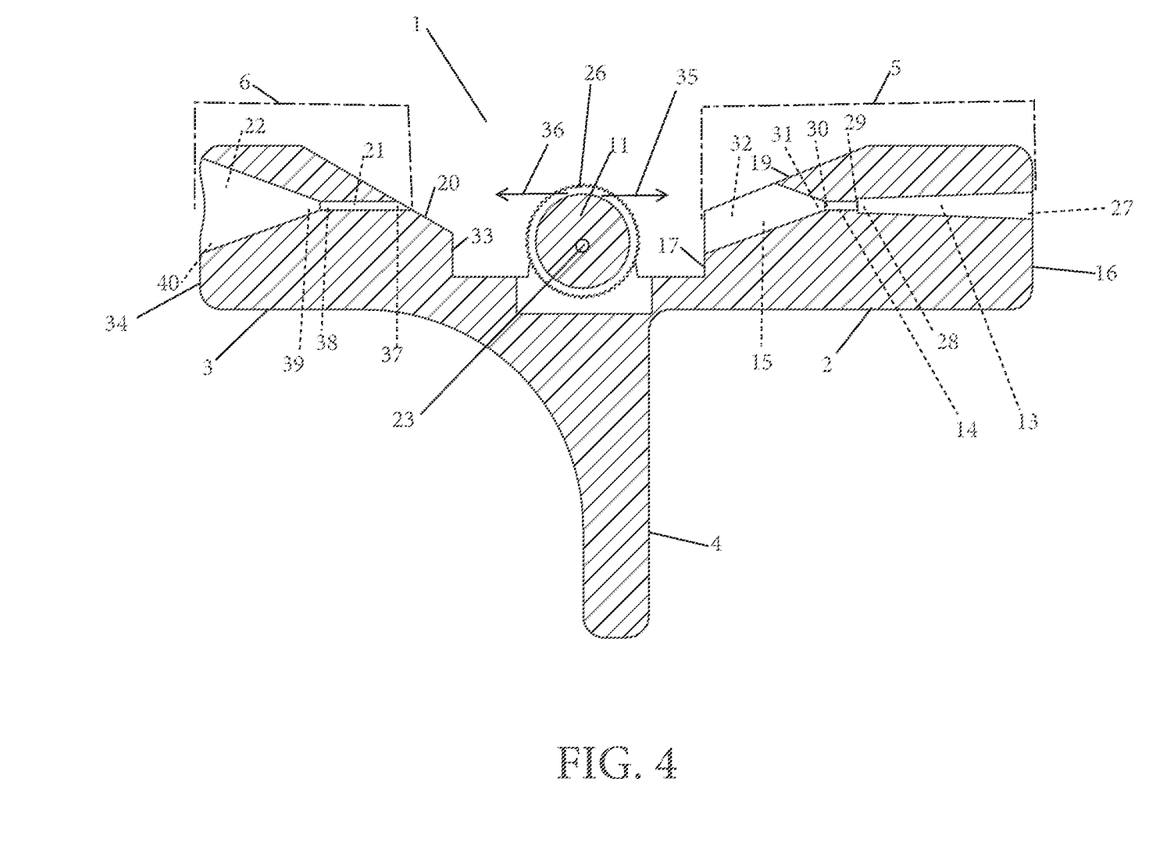
FIG. 4 is a side cut-away view of the novel guidewire retraction device.
Figure 5:
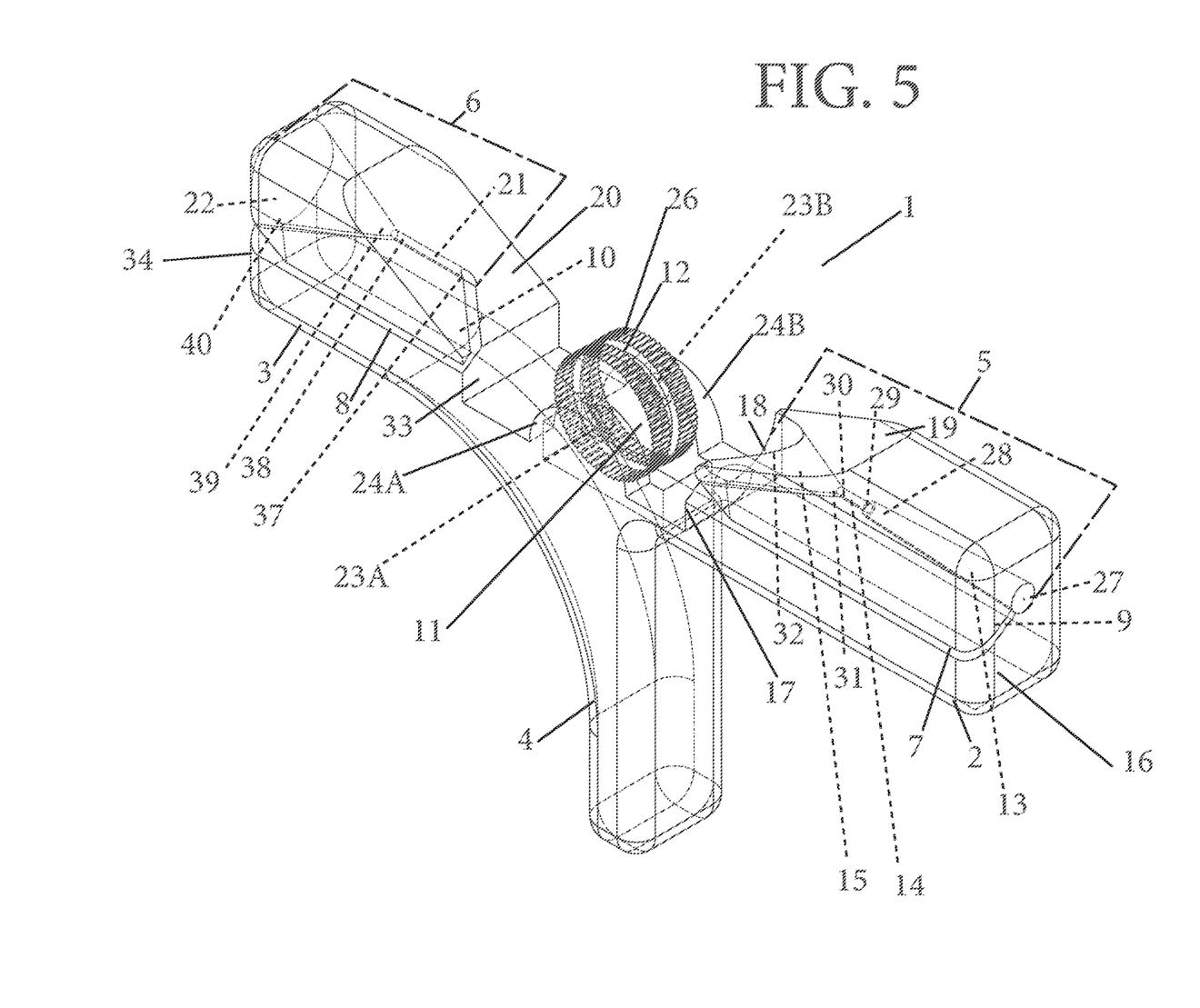
FIG. 5 is a sectional view of the distal end of the novel guidewire retraction device.
Figure 6:
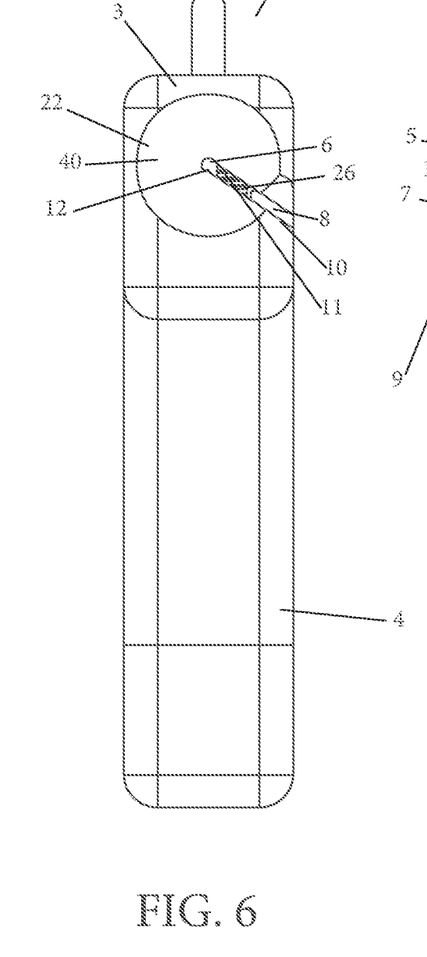
FIG. 6 is a front view of the proximal end of the novel guidewire retraction device.
Figure 7:
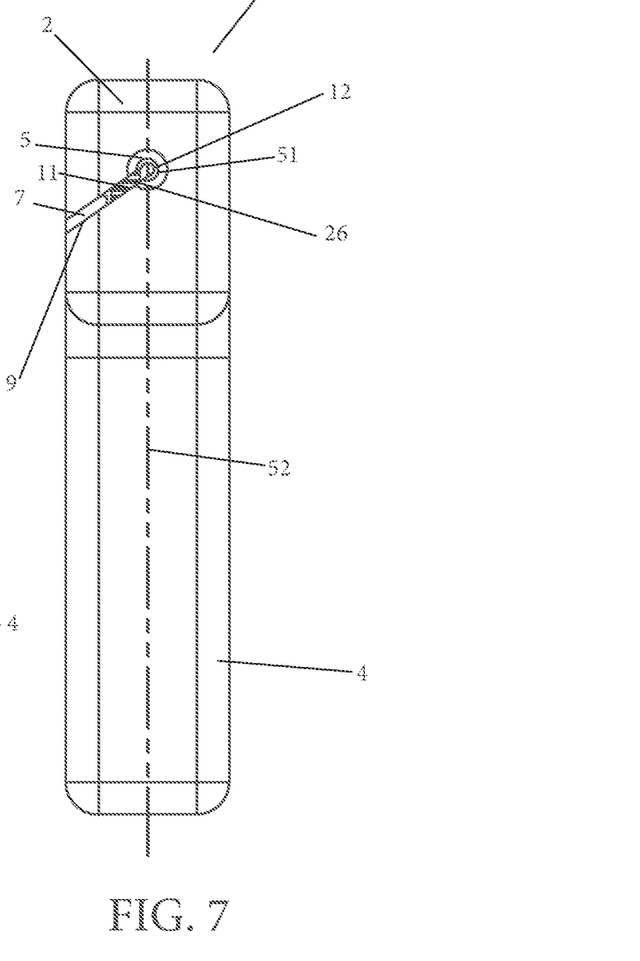
FIG. 7 is a rear view of the distal end of the novel guidewire retraction device.

FIGS. 1-7 illustrate guidewire retraction device 1 having rotation element 11. FIGS. 3-5 best depict rotation element 11 having shaft 23 (FIGS. 3-4). In particular, FIGS. 1 and 5 show first portion 23A of shaft 23 of rotation element 11 is connected to first shaft support structure 24A (FIGS. 1, 2, and 5). Second portion 23B of shaft 23 (FIG. 5) of rotation element 11 is connected to second shaft support structure 24B (FIGS. 1, 2, and 5). Referring now to FIGS. 1, 2, and 5, first shaft support structure 24A is oriented parallel to second shaft support structure 24B. Shaft 23 of rotation element 11 is connected to first support structure 24A and second support structure 24B. FIGS. 1 and 2 best show first shaft support structure 24A having a recessed portion 25 retaining first portion 23A of shaft 23 of rotation element 11.

FIGS. 1, 2, 5-7 best illustrate rotation element 11 having recess 12. Recess 12 of rotation element 11 is a track or channel that traverses the circumference of rotation element 11. It is within the scope of this invention for recess 12 of rotation element 11 to be located on a substantially central portion of rotation element 11. Recess 12 of rotation element 11 is configured to retain at least a portion of guidewire 51 (FIGS. 1-3 and 7) when guidewire 51 is retained within primary bore 5 of first support structure 2 and secondary bore 6 of second support structure 3. Rotation element 11 is configured to be rotated in first direction 35 (FIG. 4) to orient guidewire 51 in a retracted orientation. Rotation element is configured to be rotated in second direction 36 (FIG. 4) to orient guidewire 51 in an advanced orientation. FIG. 3 best shows guidewire 51 having an elevated positioning as it exits secondary bore 6 of second support structure 3 and contacts rotation element 11. As guidewire 51 is positioned through primary bore 5, guidewire 51 is oriented into a lowered position. This elevation and lowering of guidewire 51 across rotation element 11 creates tension which is a key feature of novel guidewire retention device 1 so that guidewire loss does not occur. Recess 12 of rotation element 11 is not in alignment with primary bore 5 of first support structure 2 and secondary bore 6 of second support structure 3. FIGS. 1-7 illustrate rotation element 11 having plurality of projections 26 located thereon.

FIGS. 1 and 3 illustrate guidewire retraction device 1 configured to be connected to tubing structure 46 being triple lumen catheter 46 having first lumen 47A, second lumen 47B, and third lumen 47C connected thereto. Tubing structure 46 has proximal end 49 and distal end portion 50A-50C being the distal end of lumens 47A-47C. Primary bore 5 of first support structure 2 is configured to be removably connected to proximal portion 49 of tubing structure 46. It is within the scope of this invention for distal end portion 50A-50C of tubing structure 46 to have helical threads (not shown) connected to corresponding helical threads 48 (FIGS. 8-9) of retention cap 41.

As best shown in FIGS. 3-5, guidewire retraction device 1 has first support structure 2 located opposite second support structure 3. First support structure 2 has first end 16 located opposite second end 17. First support structure 2 has primary bore 5. Primary bore 5 of first support structure 2 traverses the length of first support structure 2 from first end 16 of first support structure 2 to second end 17 of first support structure 2.

FIGS. 1, 2, 5, and 7 best depict first support structure 2 having first opening 7 bordering first ramp 9. First ramp 9 is connected to and/or in communication with primary bore 5 in such a way as to allow guidewire 51 (FIGS. 1-3) to slide out through first opening 7 of first support structure 2 and slide across the surface of first ramp 9 and be positioned out of primary bore 5 during removal of guidewire retraction device 1 from guidewire 51. Guidewire 51 is centered 52 (FIG. 7) within primary bore 5 of first support structure 2. Second support structure 3 has second opening 8 bordering second ramp 10. FIGS. 1, 2, 5, and 6 best depict second ramp 10 being connected to and/or in communication with secondary bore 6 in such a way as to allow guidewire 51 (FIGS. 1-3, and 7) to be oriented through second opening 8 of second support structure 3 and to be oriented across the surface of second ramp 10 during removal of guidewire 51 from secondary bore 6 of guidewire retraction device 1. Referring now to FIGS. 1, 2, and 5, first ramp 9 of first support structure 2 and second ramp 10 of second support structure 3 are configured to receive guidewire 51 (FIGS. 1 and 2) as guidewire 51 is being removed from both primary bore 5 and secondary bore 6 of guidewire retraction device 1 during removal of guidewire retraction device 1 from guidewire 51.

Referring now to FIGS. 4 and 5, primary bore 5 of first support structure 2 has first portion 13 being tapered. First portion 13 of primary bore 5 has first end 27 located opposite second end 28. First end 27 of first portion 13 of primary bore 5 has a diameter greater in size than second end 28 of first portion 13 of primary bore 5. First end 27 of first portion 13 of primary bore 5 is located on first end 16 of first support structure 2. Second end 28 of first portion 13 of primary bore 5 is connected to second portion 14. Second portion 14 of primary bore 5 has a constant or a non-tapered diameter that is smaller in size than second end 28 of first portion 13 of primary bore 5. Second portion 14 of primary bore 5 has first end 29 located opposite second end 30. Second end 30 of second portion 14 of primary bore 5 is connected to first end 31 of third portion 15. Third portion 15 of primary bore 5 is tapered. Third portion 15 of primary bore 5 has first end 31 located opposite second end 32. First end 31 of third portion 15 of primary bore 5 has a diameter smaller in size than second end 32 of third portion 15 of primary bore 5 due to the tapered configuration. Further, radiused edge 18 (FIGS. 1, 2, and 5) borders second end 32 of third portion 15 of primary bore 5. Second end 32 of third portion 15 of primary bore 5 is located on second end 17 of first support structure 2. FIGS. 1-5 show second end 17 of first support structure 2 having first bevel 19.

Referring again to FIGS. 4 and 5, secondary bore 6 of second support structure 6 has fourth portion 21 having first end 37 located opposite second end 38. Second end 38 of fourth portion 21 of secondary bore 6 is connected to first end 39 of fifth portion 22. Fifth portion 22 of secondary bore 6 is tapered. Fifth portion 22 of secondary bore 6 has first end 39 located opposite second end 40. First end 39 of fifth portion 22 of secondary bore 6 is connected to second end 38 of fourth portion 21 of secondary bore 6. First end 39 of fifth portion 22 of secondary bore 6 has a diameter smaller in size than a diameter of second end 40 of fifth portion 22 of secondary bore 6. Second end 40 of fifth portion 22 of secondary bore 6 is located on second end 34 of second support structure 3. FIGS. 1-5 illustrate first end 33 of second support structure 3 having bevel 20.

Figure 8:
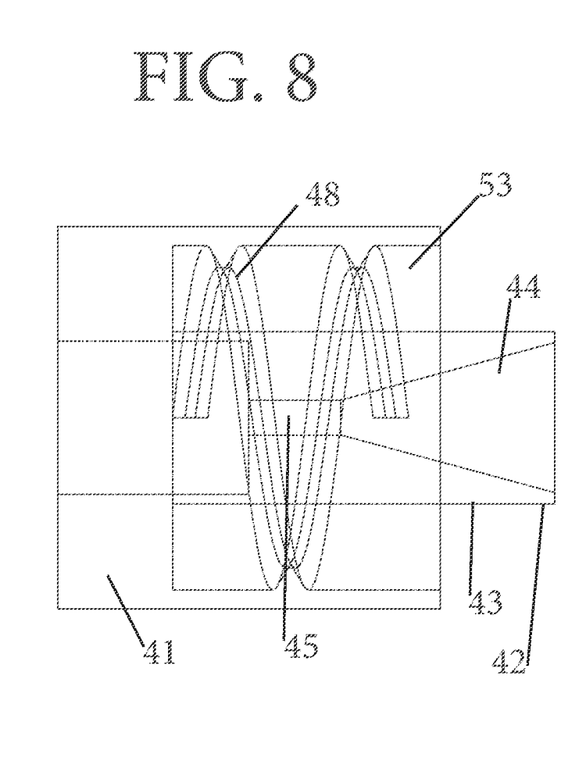
FIG. 8 is a sectional view of the novel retention cap having a threaded portion.
Figure 9:
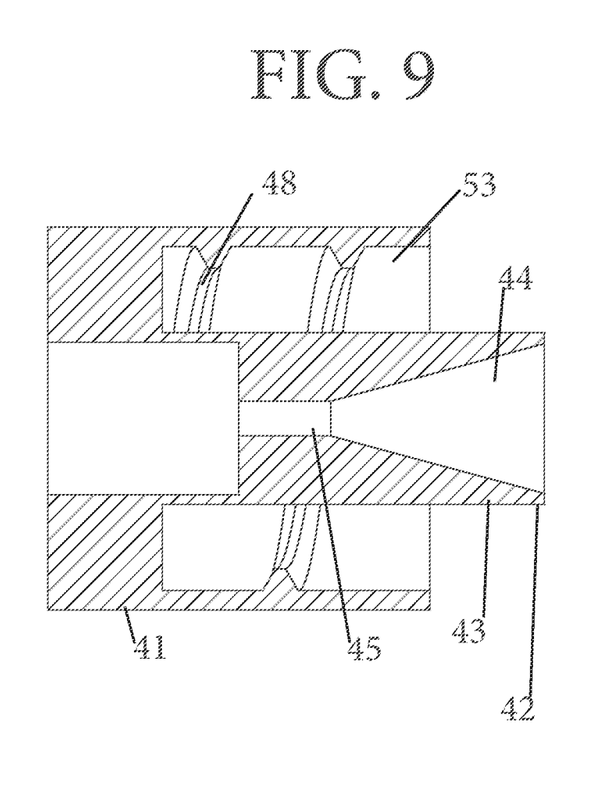
FIG. 9 is a cut-away view of the novel retention cap having a capture structure with tapered sidewalls forming a compartment; and, FIG. 10 is a block diagram of the novel steps of performing a central venous cannulation procedure.

FIGS. 1 and 3 illustrate a guidewire retraction system having guidewire retraction device 1 and retention cap 41. Retention cap 41 is configured to be connected to distal portion 50B of tubing structure 46. It is within the scope of this invention for a plurality of retention caps (not shown) to each be connected to a plurality of tubing materials including, but not limited to, each distal end of a lumen portion of a catheter. It is also within the scope of the current invention for retention cap 41 to be removably connected to at least one distal end of a lumen of a triple lumen catheter. FIGS. 1, 3, and 8-9 show retention cap 41 having integrally formed capturing structure 42. Capturing structure 42 has sidewall 43 forming compartment 44. Sidewall 43 is configured to guide an end of guidewire 51 into compartment 44. Retention cap 41 has substantially central bore 45 (FIGS. 3, and 8-9) located within compartment 44 of capturing structure 42. Substantially central bore 45 traverses the length of retention cap 41. Capturing structure 42 protrudes from retention cap 41. It is within the scope of this invention for at least a portion of capturing structure 42 to extend beyond threaded portion 48 of retention cap 41. Referring now to FIGS. 8-9, thread 48 of retention cap 41 configured to secure to the threads (not shown) of distal portion (not shown) of lumen of a catheter (not shown). Threaded portion 48 of retention cap 41 helically surrounds at least a portion of capturing structure 42. Threaded portion 48 of retention cap 41 is not located on the outer wall surface of sidewall 43 of capturing structure 42. Retention cap 41 has chamber 53. Chamber 53 has an inner wall surface having helical threads located thereon. Chamber 53 is configured to receive at least a portion of a threaded distal end (not shown) of the tubing structure (not shown).

Figure 10:
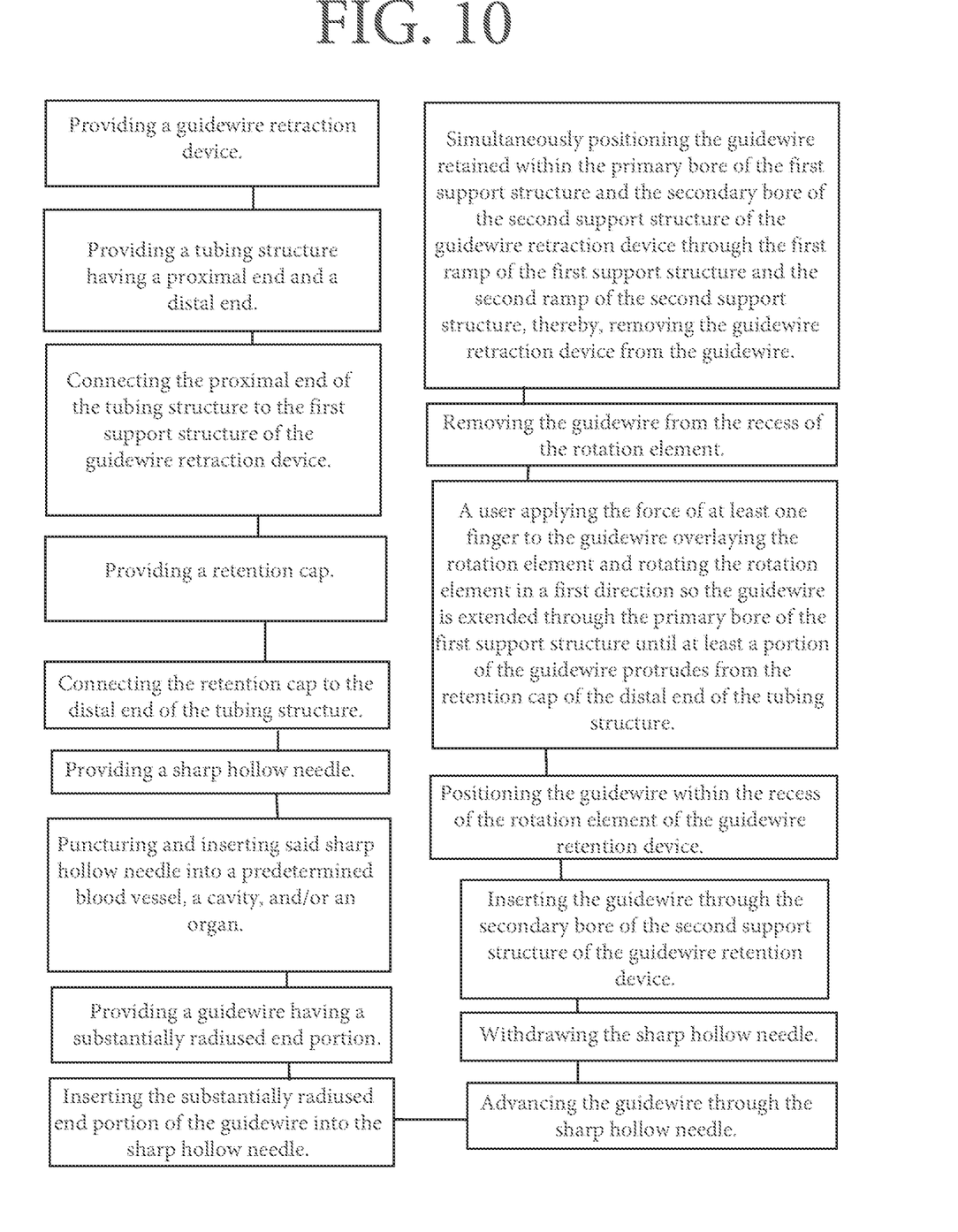

Referring now FIG. 10, a method of performing a central venous cannulation procedure has the steps of first providing guidewire retraction device 1 as shown and described in FIGS. 1-7. In the second step, any tubing structure 46 including, but not limited to, a triple lumen catheter 46 illustrated in FIGS. 1 and 3 is provided having proximal end 49 and distal end 50. A third step teaches connecting proximal end 49 of tubing structure 46 to at least a portion of first support structure 2 of guidewire retraction device 1 (FIG. 10). It is a preferred embodiment for proximal end 49 of catheter 46 to be received by at least a portion of primary bore 5 of first support structure 2. In a fourth step, retention cap 41 (FIGS. 1, 3, 8, and 9) is provided. In a fifth step, retention cap 41 is connected to at least one distal portion of tubing structure 46. Sixth, a sharp hollow needle (not shown) is provided. Next, a user (not shown) puncturing and inserting the sharp hollow needle into a predetermined blood vessel, a cavity, and/or an organ (not shown) is performed. In an eighth step, guidewire 51 (FIGS. 1-3 and 7) having a substantially radiused end portion (not shown) is provided. In a ninth step, the substantially radiused end portion of the guidewire is inserted into the sharp hollow needle. In the next step, the guidewire is advanced through the sharp hollow needle. The eleventh step teaches withdrawing the sharp hollow needle from a patient's body.

Referring again to FIG. 10, a twelfth step teaches inserting guidewire 51 through secondary bore 6 of second support structure 3 of guidewire retraction device 1. Thirteenth, positioning guidewire 51 within recess 12 of rotation element 11 of guidewire retraction device 1. In a fourteenth step, a user (not shown) applying the force of at least one finger (not shown) to guidewire 51 overlaying rotation element 11 and rotating rotation element 11 in first direction 35 (FIG. 4) so that guidewire 51 is extended through primary bore 5 of first support structure 2 and is extended through at least one distal end 50B of tubing structure 46 until at least a portion of guidewire 51 protrudes from retention cap 41 (FIG. 3). Fifteenth, removing guidewire retraction device 1 from proximal end 49 of tubing structure 46 by including, but not limited to, twisting and/or pulling tubing structure 46 away from guidewire retraction device 1 or by disconnecting a locking mechanism (not shown). Sixteenth, removing guidewire 51 from recess 12 of rotation element 11. Seventeenth, simultaneously or sequentially positioning guidewire 51 retained within primary bore 5 of first support structure 2 and secondary bore 6 of second support structure 3 of guidewire retraction device 1 through first opening 7 bordering first ramp 9 of first support structure 2 and second opening 8 bordering second ramp 10 of second support structure 3, thereby, removing and/or uninstalling guidewire retraction device 1 from guidewire 51.

It will thus be seen that the objects set forth above, and those made apparent from the foregoing description, are efficiently attained. Since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention that, as a matter of language, might be said to fall therebetween.

The invention claimed is:
1. A guidewire retraction device, comprising:
 a first support structure located opposite a second support structure, said first support structure having a first end located opposite a second end, said first support structure having a primary bore, said primary bore of said first support structure is configured to be removably connected to a proximal portion of a tubing structure, said primary bore of said first support structure traversing a length of said first support structure from said first end of said first support structure to said second end of said first support structure, said first support structure having a first opening bordering a first ramp, said first ramp of said first support structure is connected to said primary bore of said first support structure;

said second support structure having a secondary bore, said secondary bore of said second support structure traversing a length of said second support structure from a first end of said second support structure to a second end of said second support structure, said second support structure having a second opening bordering a second ramp, said second ramp of said second support structure is connected to said secondary bore of said second support structure;

said first ramp of said first support structure and said second ramp of said second support structure are configured to receive a guidewire;

a rotation element, said rotation element having a shaft, said rotation element having a recess, said recess traverses a circumference of said rotation element, said recess of said rotation element is configured to retain at least a portion of said guidewire when said guidewire is retained within said primary bore of said first support structure and said secondary bore of said second support structure, said rotation element is configured to be rotated in a first direction to orient said guidewire in a retracted orientation, said rotation element is configured to be rotated in a second direction to orient said guidewire in an advanced orientation, said recess of said rotation element is oriented in an elevated position in relation to said primary bore of said first support structure and said secondary bore of said second support structure;

said primary bore of said first support structure has a first portion being tapered, said first portion of said primary bore has a first end having a first diameter located opposite a second end having a second diameter, said first diameter of said first end of said first portion of said primary bore being greater in size than said second diameter of said second end of said first portion of said primary bore, said first end of said first portion of said primary bore is located on said first end of said first support structure, said second end of said first portion of said primary bore is connected to a second portion, an entire length of said second portion of said primary bore has a third diameter that is smaller in size than said second diameter of said second end of said first portion of said primary bore, said second portion of said primary bore is connected to a third portion, said third portion of said primary bore is tapered, said third portion of said primary bore has a first end having a fourth diameter located opposite a second end having a fifth diameter, said fourth diameter of said first end of said third portion of said primary bore being smaller in size than said fifth diameter of said second end of said third portion of said primary bore, said second end of said third portion of said primary bore is located on said second end of said first support structure; and a first shaft support structure oriented parallel to a second shaft support structure, said shaft of said rotation element is connected to said first support structure and said second support structure.

2. The guidewire retraction device of claim 1, further comprising:
a handle.

3. The guidewire retraction device of claim 1, further comprising:
said guidewire retraction device having said first portion, said second portion, said third portion, a fourth portion, and a fifth portion, whereby, said primary bore of said first support structure having said first portion, said second portion, and said third portion, said secondary bore of said second support structure having said fourth portion having a first end located opposite a second end, said second end of said fourth portion of said secondary bore of said second support structure is connected to said fifth portion, said fifth portion of said secondary bore of said second support structure is tapered, said fifth portion of said secondary bore of said second support structure has a first end having a sixth diameter located opposite a second end having a seventh diameter, said first end of said fifth portion of said secondary bore of said second support structure is connected to said second end of said fourth portion of said secondary bore of said second support structure, said sixth diameter of said first end of said fifth portion of said secondary bore of said second support structure being smaller in size than said seventh diameter of said second end of said fifth portion of said secondary bore of said second support structure, said second end of said fifth portion of said secondary bore is located on said second end of said second support structure.

4. The guidewire retraction device of claim 1, further comprising:
a first portion of said shaft of said rotation element is connected to said first shaft support structure, a second portion of said shaft of said rotation element is connected to said second shaft support structure.

5. The guidewire retraction device of claim 1, further comprising:
said rotation element having a plurality of projections located thereon.

6. The guidewire retraction device of claim 1, further comprising:
said second end of said first support structure having a bevel.

7. The guidewire retraction device of claim 1, further comprising:
said first end of said second support structure having a bevel.

8. A guidewire retraction system, comprising:
a guidewire retraction device, comprising:
a first support structure located opposite a second support structure, said first support structure having a first end located opposite a second end, said first support structure having a primary bore, said primary bore of said first support structure is removably connected to a proximal portion of a tubing structure, said primary bore of said first support structure traversing a length of said first support structure from said first end of said first support structure to said second end of said first support structure, said first support structure having a first opening bordering a first ramp, said first ramp of said first support structure is connected to said primary bore of said first support structure;

said second support structure having a secondary bore, said secondary bore of said second support structure traversing a length of said second support structure from a first end of said second support structure to a second end of said second support structure, said second support structure having a second opening bordering a second ramp, said second ramp of said second support structure is connected to said secondary bore of said second support structure;

said first ramp of said first support structure and said second ramp of said second support structure are configured to receive a guidewire;

a rotation element, said rotation element having a shaft, said rotation element having a recess, said recess traverses a circumference of said rotation element, said recess of said rotation element is configured to retain at least a portion of said guidewire when said guidewire is retained within said primary bore of said first support structure and said secondary bore of said second support structure, said rotation element is configured to be rotated in a first direction to orient said guidewire in a retracted orientation, said rotation element is configured to be rotated in a second direction to orient said guidewire in an advanced orientation, said recess of said rotation element is oriented in an elevated position in relation to said primary bore of said first support structure and said secondary bore of said second support structure; and, a first shaft support structure oriented parallel to a second shaft support structure, said shaft of said rotation element is connected to said first support structure and said second support structure;

said primary bore of said first support structure has a first portion being tapered, said first portion of said primary bore has a first end having a first diameter located opposite a second end having a second diameter, said first diameter of said first end of said first portion of said primary bore being greater in size than said second diameter of said second end of said first portion of said primary bore, said first end of said first portion of said primary bore is located on said first end of said first support structure, said second end of said first portion of said primary bore is connected to a second portion, an entire length of said second portion of said primary bore has a third diameter that is smaller in size than said second diameter of said second end of said first portion of said primary bore, said second portion of said primary bore is connected to a third portion, said third portion of said primary bore is tapered, said third portion of said primary bore has a first end having a fourth diameter located opposite a second end having a fifth diameter, said fourth diameter of said first end of said third portion of said primary bore being smaller in size than said fifth diameter of said second end of said third portion of said primary bore, said second end of said third portion of said primary bore is located on said second end of said first support structure; and a retention cap, said retention cap is configured to be connected to a distal portion of said tubing structure; said retention cap having a capturing structure, said capturing structure having a sidewall forming a compartment, said sidewall is configured to guide said guidewire into said compartment, said retention cap having a substantially central bore connected to said compartment of said capturing structure, said substantially central bore traversing at least a portion of a length of said retention cap.

9. The guidewire retraction system of claim 8, further comprising:
said substantially central bore of said retention cap is configured to have a diameter large enough in size for said guidewire to be received by said substantially central bore and having said diameter small enough in size for said guidewire to traverse said length of said retention cap by a force of a user.

10. The guidewire retraction system of claim 8, further comprising:
at least a portion of said retention cap having a pliable material configured to conform to an outer surface of said guidewire.

11. The guidewire retraction system of claim 8, further comprising:
said secondary bore of said second support structure has a fourth portion having a first end located opposite a second end, said second end of said fourth portion of said secondary bore is connected to a fifth portion, said fifth portion of said secondary bore is tapered, said fifth portion of said secondary bore has a first end having a sixth diameter located opposite a second end having a seventh diameter, said first end of said fifth portion of said secondary bore is connected to said second end of said fourth portion of said secondary bore, said sixth diameter of said first end of said fifth portion of said secondary bore being smaller in size than said seventh diameter of said second end of said fifth portion of said secondary bore, said second end of said fifth portion of said secondary bore is located on said second end of said second support structure.

12. The guidewire retraction system of claim 8, further comprising:
a first portion of said shaft of said rotation element is connected to said first shaft support structure, a second portion of said shaft of said rotation element is connected to said second shaft support structure.

13. The guidewire retraction system of claim 8, further comprising:
said rotation element of said guidewire retraction device having a plurality of projections located thereon.

14. The guidewire retraction system of claim 8, further comprising:
said second end of said first support structure of said guideline retraction device having a bevel.

15. The guidewire retraction system of claim 8, further comprising:
said first end of said second support structure of said guideline retraction device having a bevel.

16. The guidewire retraction system of claim 8, further comprising:
said capturing structure protrudes from an end of said retention cap.

17. The guidewire retraction system of claim 8, further comprising:
said retention cap having a threaded portion, said threaded portion of said retention cap is configured to connect to a threaded portion of said distal portion of said tubing structure.

* * * * *